United States Patent [19]

Weiner

[11] 4,213,460
[45] Jul. 22, 1980

[54] TICK REMOVING FORCEPS

[76] Inventor: Israel H. Weiner, 3406 Keyser Rd., Baltimore, Md. 21208

[21] Appl. No.: 943,483

[22] Filed: Sep. 18, 1978

Related U.S. Application Data

[63] Continuation-in-part of Ser. No. 753,813, Dec. 23, 1976, abandoned.

[51] Int. Cl.$^2$ ............................................. A61B 17/50
[52] U.S. Cl. .............................. 128/303 R; 128/303.1; 128/355; 128/399; 43/134; 43/144; 119/87; 219/230
[58] Field of Search .................. 128/1 R, 303 R, 303.1, 128/303.14, 303.17, 321, 324, 354, 355, 399, 400, 794, 800, 801; 43/134, 144; 119/87; 81/43; 219/221, 227, 230

[56] References Cited

U.S. PATENT DOCUMENTS

| 210,163 | 11/1878 | Steinmetz | 43/134 |
|---|---|---|---|
| 702,472 | 6/1902 | Pignolet | 128/303.1 |
| 728,883 | 5/1903 | Downes | 128/303.1 |
| 1,422,826 | 7/1922 | Brown | 219/230 |
| 2,176,479 | 10/1939 | Willis | 128/303.13 |
| 2,533,947 | 12/1950 | Lipnicki et al. | 219/227 |
| 2,894,512 | 7/1959 | Tapper | 128/355 X |
| 3,911,241 | 10/1975 | Jarrard | 128/303.17 X |
| 4,096,864 | 6/1978 | Kletshka et al. | 128/354 |

FOREIGN PATENT DOCUMENTS

| 171079 | 6/1965 | U.S.S.R. | 128/303.14 |
| 401328 | 2/1974 | U.S.S.R. | 43/144 |

Primary Examiner—Lee S. Cohen
Attorney, Agent, or Firm—Finnegan, Henderson, Farabow, Garrett & Dunner

[57] ABSTRACT

Forceps including a pair of closable arms having cup-shaped gripping members affixed to the ends of the arms and adapted to be closed upon and to grip the protruding portion of a tick or other parasite which is attached through biting engagement to the skin of a host animal. At least one of the gripping members is provided with either an electrical thermal element or a chemical agent applicator affixed to its inner surface and adapted, when applied to a tick or parasite, to cause the latter to release its bite whereupon it can be easily, hygienically, and painlessly removed from the skin of the host animal by a retraction force applied via the forceps.

21 Claims, 8 Drawing Figures

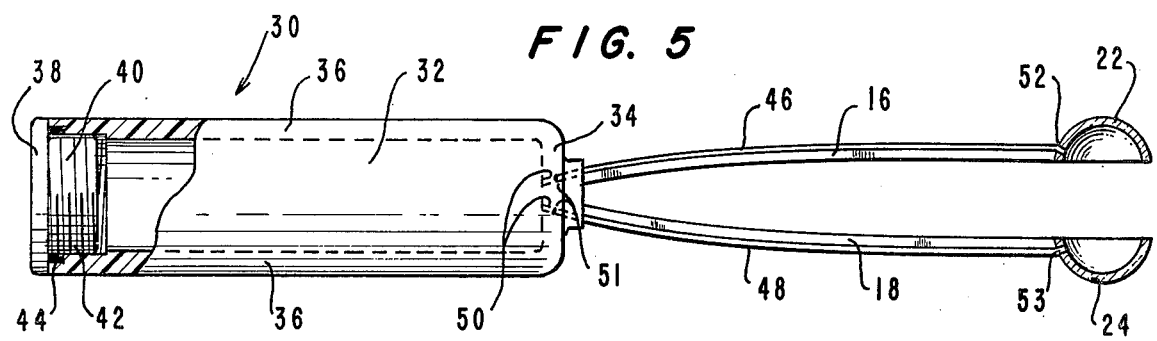
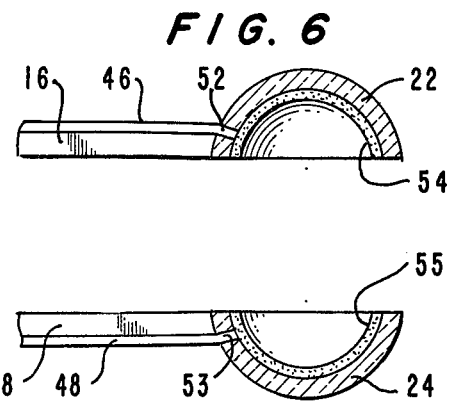
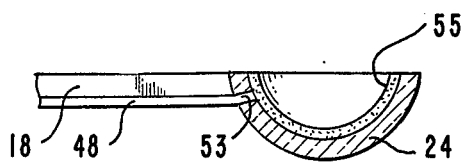
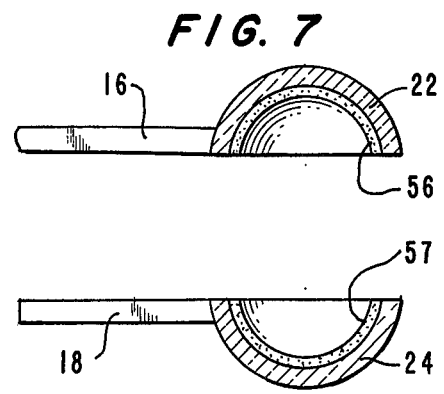
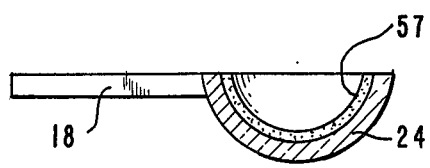
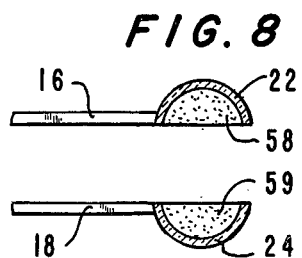
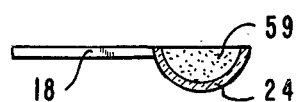

TICK REMOVING FORCEPS

BACKGROUND OF THE INVENTION

The present application is a continuation-in-part of U.S. application Ser. No. 753,813, filed on Dec. 23, 1976, now abandoned.

This invention relates to surgical instruments and, more particularly, to a forceps adapted for use in hygienically removing parasitic organisms attached to the skin of a host animal.

One type of parasite for which the forceps of the invention is particularly well suited is the common tick. Ticks are geographically distributed throughout most of the United States and, in various species, across many other areas of the world. These various tick species are vectors for the transmission of many serious diseases, including Rocky Mountain Spotted Fever in the Western Hemisphere and various related rickettsial diseases in the Mediterranean area, Africa, Australia, India, Russia and elsewhere.

Ticks attach themselves to the skin of humans and animals, biting into the skin and feeding on the blood of the host animal and, if infected, can transmit disease to the host animal. Imbedded ticks should be removed from the skin with care to avoid crushing the tick, which may release contaminated material, and to prevent leaving tick mouth parts imbedded in the skin. Removal of engorged ticks with bare fingers is dangerous since infection through unbroken skin is believed to be possible.

OBJECTS AND SUMMARY OF THE INVENTION

It is a primary object of this invention to provide an improved device for simply, hygienically and painlessly removing ticks and other parasitic organisms attached to the skin of a host animal.

It is a further object to provide an instrument of the type described which is compact, inexpensive and easy to operate.

Another object is to provide an instrument of the type described which is highly reliable and which may be ruggedly constructed so that it can be conveniently taken on camping and hiking trips and the like and which may be used in remote environments where electrical outlets are not available.

Additional objects and advantages of the invention will be set forth in part in the description which follows, and in part will be apparent from the description, or may be learned by practice of the invention. The objects and advantages of the invention may be realized and attained by means of the instrumentalities and combinations particularly pointed out in the appended claims.

To achieve the foregoing objects and in accordance with the purpose of the invention, as embodied and broadly described herein, the instrument of the present invention comprises a forceps, mutually opposed gripping means attached to the forceps so as to be brought together on actuation of the forceps, the gripping means including a concave surface portion to at least partially enclose the protruding portion of a parasitic organism, and relaxant means provided on at least one of the gripping means for applying to the body of a parasitic organism an agent for causing the organism to relax its bite when the gripping means are engaged with the parasitic organism, enabling the parasitic organism to be removed from the host animal by a retraction force applied via the gripping means.

In a first exemplary embodiment of the present invention the relaxant means comprises heating means mounted in a position to apply heat to the enclosed portion of the parasitic organism. This exemplary embodiment may further include a control means for activating the heating means when the gripping means are brought together to engage the parasitic organism and for allowing the heating means to be deactivated when the apparatus is not in use.

In a second exemplary embodiment, the relaxant means comprises means for applying a relaxant agent in the form of a chemical substance to the body of the parasitic organism. This second exemplary embodiment may include an absorbent material mounted on an internal surface of at least one of the gripping means and a supply means to apply the relaxant chemical agent to the absorbent material.

The accompanying drawings, which are incorporated with and constitute a part of the specification, illustrate exemplary embodiments of the invention and, together with the description, serve to explain the principles of the invention.

BRIEF DESCRIPTION OF THE DRAWINGS

FIG. 5 illustrates another embodiment of the forceps instrument of the invention which is adapted to apply a chemical substance to the tick prior to its removal.

FIG. 6 is a center cross-section view of the end portion of a modified version of the forceps of FIG. 5 and illustrates the use of an absorbent, sponge-like material inside the gripping members of the forceps.

FIG. 7 is a cross-section view similar to FIG. 6 and illustrates another embodiment of the forceps utilizing a chemical substance.

FIG. 8 is a cross-section view of the gripping members and illustrates still another means for applying a chemical substance to the body of the tick.

DETAILED DESCRIPTION OF EMBODIMENTS

Figure 1:
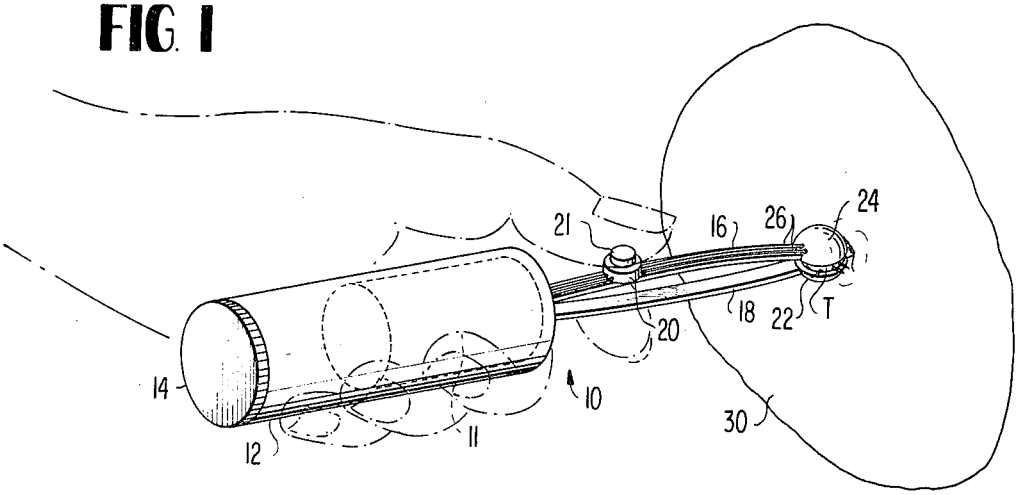
FIG. 1 illustrates one embodiment of a heat-applying tick removing forceps in accordance with the invention and shows the manner in which it is adapted to be utilized by an operator.

Reference will now be made in detail to the present preferred embodiments of the invention, examples of which are illustrated in the accompanying drawings.

In accordance with the invention, a forceps is provided for closing upon and gripping the protruding portion of the tick or other parasite. As here embodied and shown in FIG. 1, the forceps comprise a pair of closable arms 16 and 18 which may be constructed of spring stainless steel or other suitable material.

Additionally, in accordance with the invention, mutually opposed gripping means are affixed to the forceps arms and are constructed to at least partially enclose the protruding portion of the parasite. As herein embodied, such gripping means includes a pair of oppositely aligned cup-shaped members 22 and 24 affixed to the tips of the forceps arms 18 and 16, respectively. The members 22 and 24 may be formed as an integral part of the arms 16 and 18 or may be separate elements affixed to the arms by an appropriate joining method such as crimping, gluing, welding, brazing or the like. The gripping members 22 and 24 are sized such that their inner surfaces may be brought into contact with the body parts of the protruding portion of the parasite when gentle squeezing pressure is applied through the arms of the forceps.

Further in accordance with the invention relaxant means are provided on at least one of the gripping means for applying to the body of the parasite an agent for causing the parasite to relax its bite when the gripping means are engaged therewith. As embodied in a first exemplary embodiment, the relaxant means comprises heating means mounted on the gripping means and adapted to apply heat to the parasite so that it releases its bite. Such heating means may include a thermal element such as an electrical resistance unit 28 (FIGS. 3 and 4) mounted on an inside surface of one of the gripping members. The thermal element is of conventional design and therefore detailed disclosure thereof is omitted. The element may, for example, comprise a wire-wound filament encased in an insulating material or may include a plated film resistance element carried on a suitable substrate.

Further in accordance with this exemplary embodiment, the heating means includes a power supply in the form of a conventional battery 11 (FIG. 1) mounted within casing member 12 and connected to appropriate electrical contact elements (not shown). A threaded cap 14 is provided at the end of the casing member to permit easy removal and changing of the battery. The casing member also serves as a handle by which the operator may grip the forceps 16, 18.

Additionally, control means are provided for activating the heating element when the gripping members are brought into engagement with the protruding portion of the parasite. Pursuant to the instant embodiment, such control means comprises a switch 20 (FIG. 1) mounted on the outer surface of arm 16. A pair of conductors 26 connect the thermal element associated with gripping member 24 in circuit with the battery contacts in casing 12. The switch 20 is positioned such that the thumb or other finger of the operator presses on the switch actuator 21 in the act of applying pressure to close the forceps arms. Conductors 26 may be enclosed within the arm 16 or may be carried on the outer surface thereof as shown in FIG. 1 and protected by an insulating sleeve or other appropriate protective member.

In operation, the operator holds the casing 12 and squeezes the arms of the forceps between the thumb and forefinger as shown in FIG. 1 (the thumb resting on the switch actuator 21). Pressure is applied to close the gripping members 22 and 24 on the protruding portion of the tick T which is attached to and possibly partially embedded in the skin 30 of a person or animal. As this operation is performed, the applied pressure closes switch 20 and the thermal element associated with gripping member 24 is energized to apply heat to the body of the tick and this induces the tick to relax its bite. The operator may then, through a gentle pulling and lifting motion, cleanly and painlessly withdraw the tick.

Figure 2:
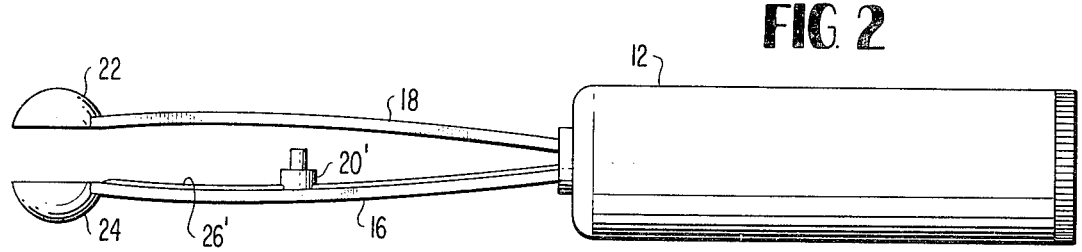
FIG. 2 illustrates another embodiment of the heat-applying forceps instrument of the invention.

An alternate arrangement of the first exemplary embodiment is shown in FIG. 2 wherein a control switch 20' is mounted on an inside surface of forceps arm 16. Conductors 26' which connect the thermal element in gripping member 24 to the battery are carried on the inside surface of the arm. With this arrangement the operator does not place a finger directly in contact with the switch but instead the switch actuator is depressed through engagement with the opposing forceps arm 18 when the forceps are closed.

Figure 3:
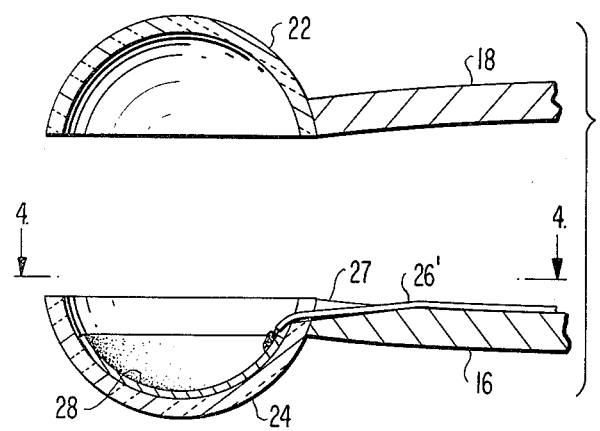
FIG. 3 is a center cross-section view of the end portion of the forceps of FIG. 2 and illustrates an embodiment of the invention in which a thermal element is incorporated in one of the forceps gripping members.
Figure 4:
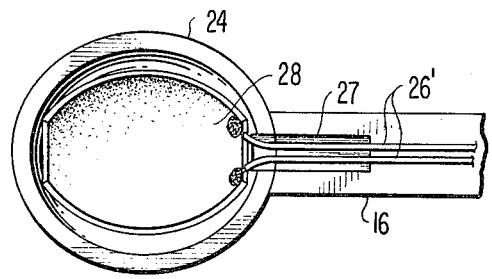
FIG. 4 is a view of one of the gripping members taken along the line 4—4 of FIG. 3.

As shown in FIGS. 3 and 4, the thermal element 28 is configured roughly in the form of a hemispherical segment which conforms to the shape of the inner surface of the cup-shaped gripping member 24. Conductors 26' are electrically connected to the thermal element at terminal points adjacent to arm 16. As shown, a groove 27 may be provided in arm 16 and in the edge of gripping member 24 to permit entry of the conductors 26' into the area were contact is made.

Gripping members 22 and 24 are preferably fabricated of a thermally insulative material so that excessive heat is not applied to the patient's skin during the parasite removal operation. Members 22 and 24 may be integrally molded or formed out of the insulative material or the latter may be applied in the form of a coating to the outer surface of the gripping members. While thermal insulation may be used only on the gripping member which supports the heating element, it may be desirable to use thermal insulation with both gripping members.

It has been found that the application of a relaxant chemical agent to the protruding portion of a parasitic organism can also cause the organism to relax its bite. In particular it has been found that alcohol, gasoline and kerosine exhibit such relaxant characteristics. Therefore, as embodied in a second exemplary embodiment of this invention, the relaxant means comprises means for applying the relaxant agent in the form of a chemical substance to the body of the parasitic organism. FIGS. 5 through 8 illustrate several arrangements of this second exemplary embodiment. In all of these views the gripping members are shown in cross-section to more clearly illustrate the form of the relaxant means.

In FIG. 5, a cylindrically shaped handle portion 30 is preferably formed of a flexible material such as rubber or a well known flexible plastic. Handle portion 30 includes a flexible reservoir 32 for containing a supply of relaxant chemical agent. The flexible reservoir 32 is formed by the front end wall 34, side wall 36, and end stopper 38 of the handle 30. As shown, the end stopper 38 is attached to the side wall 36 through threaded engagement of the neck 40 of end stopper 38 and threaded opening 42. A sealing washer 44 may be provided between the end stopper 38 and the side wall 36 to prevent leakage of any chemical agent carried by the flexible reservoir.

Two tubes, 46 and 48, interconnect the flexible reservoir 32 and the gripping members 22 and 24. These tubes, 46 and 48, pass through holes 50 in end wall 34 of handle 30 and through holes 52 and 53 in the gripping members 22 and 24, respectively. Tubes 46 and 48 thereby form a leakproof channel for carrying a chemical agent from the flexible reservoir 32 to the gripping members 22 and 24. Valves 51 may be provided in passages 50 to prevent leakage of the chemical agent from reservoir 32 when the reservoir is in its normal, non-deformed state but allow the flow of the agent from the flexible reservoir 32 through tubes 46 and 48 to members 22 and 24 when an operator of the device squeezes the reservoir. When the reservoir is so squeezed, the chemical agent flows through holes 52 and 53 of members 22 and 24, respectively, and is applied to the parasitic organism enclosed in the members 22 and 24.

FIG. 6 shows an alternative arrangement of gripping members that can be used with the apparatus shown generally in FIG. 5. As shown, layers of sponge-like absorbent material 54 and 55 are attached to the inner surfaces of the gripping members 22 and 24 by well known means such as adhesives. The absorbent material 54 may be organic or synthetic material, such as sponge or foam material, and is preferably configured roughly in the form of a hemispherical segment which conforms to the shape of the inner surface of the cup-shaped gripping members 22 and 24. In practice, a supply of relaxant chemical agent flows through tubes 46 and 48 to the absorbent material 54 and 55, which in turn, upon contact with the parasitic organism, applies the chemical agent to the protruding portion of the organism.

The operation of the embodiment shown in FIGS. 5 and 6 is substantially as follows. An operator first fills the flexible reservoir 32 with a relaxant chemical substance such as alcohol, gasoline or kerosine. He does so by first removing the end stopper 38, pouring the chemical substance into the reservoir 32 and then sealing the reservoir by replacing the end stopper 38. The operator then holds the handle 36 loosely and squeezes the arms of the forceps between the thumb and forefinger in the same manner shown in FIG. 1. Pressure is applied to close the gripping members 22 and 24 on the protruding portion of a parasitic organism which is attached to and possibly partially embedded in the skin of a host person or animal. Once the gripping members 22 and 24 gently enclose the protruding portion of the organism, the operator applies a slight pressure with his hand to squeeze the flexible reservoir 32 and thereby either (1) apply the relaxant chemical substance directly to the organism (FIG. 5), or (2) saturate the absorbent material 54, 55 and thereby indirectly apply the agent to the organism. (FIG. 6). The chemical agent once so applied to the organism causes the organism to relax its bite. The operator may then, through a gentle pulling and lifting motion, cleanly and painlessly withdraw the tick.

FIGS. 7 and 8 show two additional arrangements of the second exemplary embodiment. In both FIGS. 7 and 8 the apparatus includes a forceps comprising arms 16 and 18, which are joined to a suitable handle portion. In these two forms, the handle portion of the apparatus does not include a flexible reservoir for obtaining a supply of relaxant chemical substance.

As shown in FIG. 7, layers of absorbent material 56 and 57 are attached to the inner surfaces of gripping members 22 and 24, respectively. This material 56 is of the same material and shape as earlier described in reference to FIG. 6. Alternatively, the absorbent material may be shaped in the form of two substantially solid hemispheres as shown in FIG. 8. In the latter embodiment the absorbent material is resilient enough to conform to the shape of the organism when the forceps are closed about the organism. In both the embodiments shown in FIGS. 7 and 8, a gentle squeezing of the gripping members about the parasitic organism brings the absorbent material 56, 57 or 58, 59 in contact with the parasitic organism and induces the application of the relaxant chemical substance to the organism.

In the operation of the arrangements of the second exemplary embodiment shown in FIGS. 7 and 8, the operator immediately before applying the forceps to the parasitic organism, dips the gripping members 22 and 24 into a supply of relaxant chemical substance. The absorbent materials 56, 57 or 58, 59 thereby become saturated with the relaxant chemical agent to apply that agent upon contact with the organism. The operator squeezes the arms 16 and 18 of the forceps in the same manner shown in FIG. 1 and applies sufficient pressure to close the gripping members on the portion of the parasitic organism. Upon contact with the organism, the saturated absorbent materials apply relaxant chemical substance to the organism. The chemical substance causes the organism to relax its bite, and the operator may then, through a general pulling and lifting motion, cleanly and painlessly withdraw the tick.

It is thus seen that the forceps instrument of the invention enables removal of an attached tick or other parasite through controlled pressure and without direct contact with the parasite, thus reducing the possibility of crushing the body during removal and minimizing the risk of infection. Heat, a chemical substance, or other relaxant means are applied to the parasite to facilitate release without risking additional skin injury to the patient. The instrument is small, easily portable and inexpensive to fabricate and may be easily and safely used even by untrained persons. Discomfort and risk inherent in removal of the parasite is minimized both for the patient and for the operator. While the above-described thermal embodiment calls for a battery power supply, it is readily apparent that a plug-in adaptor circuit may be provided to enable operation of the device from a conventional household A.C. power source.

It will be appreciated that various additional changes in the form and details of the above-described preferred embodiments may be effected by persons with ordinary skill without departing from the true spirit and scope of the invention.

What is claimed is:

1. Apparatus for removing a parasitic organism attached to the skin of a host animal comprising, in combination:
   a forceps;
   mutually opposed gripping means affixed to said forceps so as to be brought together on actuation of said forceps, said gripping means being shaped to at least partially enclose the protruding portion of said parasitic organism and at least a portion of said gripping means being constructed of a thermally insulative material;
   heating means mounted on said gripping means in a position to apply heat to the enclosed portion of said organism; and
   control means for activating said heating means when said gripping means are engaged with said parasitic organism, whereby said organism is induced through application of heat to release its grip on the skin of said host animal, enabling the removal of said organism with said forceps, said thermally insulative material protecting the skin of said host animal from excessive heating.

2. The apparatus set forth in claim 1 wherein said gripping means comprise a pair of cup-shaped members affixed to said forceps, the rim portions of said cup-shaped members being aligned with respect to each other so as to surround the body portion of said organism when said forceps are actuated, thereby enclosing at least a portion of said organism within said cup-shaped members.

3. The apparatus set forth in claim 1 wherein:
   said forceps comprises a pair of closable arms;

said control means includes a switch positioned between the arms of said forceps and adapted to be closed by the relative movement of said arms toward one another; and said heating means includes an electrically energizable thermal element incorporated in said gripping means and a power supply connected in circuit through said switch with said thermal element whereby the closing of said switch energizes said thermal element.

4. The apparatus set forth in claim 1 wherein said heating means comprises a battery and an electrical resistance element, the latter being mounted on a surface of said gripping means in a position to contact said protruding portion of said parasitic organism when said gripping means engage said organism.

5. The apparatus set forth in claim 1 wherein:

said forceps comprises a pair of closable arms;

said control means includes a switch positioned on one of said arms and adapted to be closed by pressure applied by an operator in closing said arms; and said heating means includes an electrically energizable thermal element incorporated in said gripping means and a power supply connected in circuit through said switch with said thermal element whereby the closing of said switch energizes said thermal element.

6. The apparatus set forth in claim 5 wherein said switch includes actuating means adapted to be engaged by the hand of an operator as the latter applies pressure to close said arms.

7. Apparatus for removing a tick attached through biting engagement to the skin of a host animal comprising, in combination:

a forceps including tip portions movable toward one another when said forceps are closed;

a pair of cup-shaped gripping members mounted on the tip portions of said forceps in opposed relation to each other and adapted when said forceps are closed to at least partially enclose the protruding portion of said tick, the outer surface of at least one of said gripping members being formed of a thermally insulative material;

a thermal element provided on an internal surface of one of said gripping members in a position to apply heat to the enclosed portion of said tick; and, selectively operable energy supply means coupled to said thermal element for energizing the latter when said gripping members are closed on said tick whereby the heat from said thermal element induces said tick to relax its bite, enabling removal of said tick from said host animal, said thermally insulative material protecting the skin of said host animal from excessive heating.

8. Apparatus for removing a tick attached through biting engagement to the skin of a host animal comprising, in combination;

a forceps having a pair of closable arms including tip portions;

a pair of cup-shaped gripping members mounted, one each, in opposed relation on said tip portions of said arms so as to at least partially enclose the protruding portion of said tick when said forceps are closed;

an electrical resistance heating element provided on an internal surface of one of said gripping members in a position to apply heat to the enclosed portion of said tick;

a battery;

electrical connections from said battery to said heating element;

a switch in said connections; and actuator means positioned between said forceps arms and adapted to engage one of said arms to operate said switch when said forceps arms are closed, whereby said heating element is energized to apply heat to said tick, inducing the latter to relax its bite to permit removal of said tick from the skin of said host animal.

9. The apparatus set forth in claim 8 further comprising:

a hollow handle member containing said battery and being affixed to said forceps at the ends thereof opposite said gripping members to facilitate the holding and manipulating of said forceps by an operator.

10. An apparatus for removing a parasitic organism attached to the skin of a host animal comprising, in combination:

forceps;

mutually opposed gripping means attached to said forceps so as to be brought together on actuation of said forceps, said gripping means including a concave surface portion to at least partially enclose the protruding portion of said parasitic organism; and relaxant means provided on at least one of said gripping means for applying to the body of said parasitic organism an agent for causing said organism to relax its bite when said gripping means are engaged with said parasitic organism, enabling said parasitic organism to be removed from said host animal by a retraction force applied via said gripping means.

11. The apparatus of claim 10 wherein said relaxant means comprises heating means mounted in a position to apply heat to the enclosed portion of said parasitic organism.

12. The apparatus of claim 11 further comprising control means for activating said heating means when said gripping means are brought together to engage said parasitic organism and for allowing said heating means to be deactivated when said apparatus is not in use.

13. An apparatus for removing a parasitic organism attached to the skin of a host animal comprising, in combination:

forceps;

mutually opposed gripping means attached to said forceps so as to be brought together on actuation of said forceps, said gripping means being shaped to at least partially enclose the protruding portion of said parasitic organism; and relaxant means provided on at least one of said gripping means for applying to the body of said parasitic organism a chemical substance for causing said organism to relax its bite when said gripping means are engaged with said parasitic organism, enabling said parasitic organism to be removed from said host animal by a retraction force applied via said gripping means.

14. The apparatus of claim 13 wherein said relaxant means further comprises an absorbent material adapted to be saturated with said chemical substance.

15. The apparatus of claim 14 wherein said chemical substance is selected from the group consisting of alcohol, gasoline, and kerosine.

16. The apparatus of claim 13 wherein said gripping means comprises a pair of cup-shaped members affixed to said forceps, the rim portions of said cup-shaped members being aligned with respect to each other so as to surround the body portion of said organism when said forceps are actuated, thereby enclosing at least a portion of said organism within said cup-shaped members.

17. An apparatus for removing a parasitic organism attached to the skin of a host animal comprising, in combination:
   a forceps;
   mutually opposed gripping means affixed to said forceps to be brought together on actuation of said forceps, said gripping means being shaped to at least partially enclose the protruding portion of said parasitic organism;
   an absorbent material mounted on an internal surface of at least one of said gripping means in a position to contact the portion of said parasitic organism enclosed by said gripping means and to apply a relaxant chemical agent thereto; and
   supply means containing a supply of said chemical agent and including means for feeding said agent to said absorbent material.

18. The apparatus of claim 17 wherein said gripping means comprises a pair of cup-shaped members affixed to said forceps, the rim portions of said cup-shaped members being aligned with respect to each other so as to surround the body portion of said organism when said forceps are actuated, thereby enclosing at least a portion of said organism within said cup-shaped members.

19. The apparatus of claim 18 wherein said forceps comprise a pair of closable arms joined by a handle portion and wherein said supply means comprises:
   a flexible reservoir attached to said forceps and adapted to be squeezed by an operator desiring to apply said chemical agent to the organism; and
   a tube interconnecting said flexible reservoir and said absorbent material.

20. An apparatus for removing a parasitic organism attached through biting engagement to the skin of a host animal comprising, in combination:
   a forceps including tip portions movable toward one another when said forceps are closed and having a handle portion;
   a pair of cup-shaped gripping members mounted on the tip portions of said forceps in opposed relation to each other and adapted when said forceps are closed to at least partially enclose the protruding portion of said organism;
   absorbent material mounted on an internal surface of at least one of said cup-shaped gripping members in a position to contact the enclosed portion of said organism when said forceps are closed;
   a flexible reservoir included in said handle portion of said forceps for containing a supply of a relaxant chemical agent; and
   a tube interconnecting said flexible reservoir and said absorbent material, whereby an operator closing said forceps on said organism can apply pressure to said reservoir to saturate said absorbent material with a quantity of said agent to apply said agent to said organism prior to removing the latter from the skin of said host animal.

21. An apparatus for removing a parasitic organism attached through biting engagement to the skin of a host animal comprising, in combination:
   a forceps including tip portions movable toward one another when said forceps are closed and having a handle portion;
   a pair of cup-shaped gripping members mounted on the tip portions of said forceps in opposed relation to each other and adapted when said forceps are closed to at least partially enclose the protruding portion of said organism;
   a flexible reservoir affixed to said handle portion of said forceps for containing a supply of a relaxant chemical agent; and
   a tube interconnecting said flexible reservoir and at least one of said cup-shaped gripping members, whereby an operator closing said forceps on said organism can apply pressure to said reservoir to apply said agent to said organism prior to removing the latter from the skin of said host animal.

* * * * *